US005888498A

United States Patent [19]
Davis et al.

[11] Patent Number: 5,888,498
[45] Date of Patent: Mar. 30, 1999

[54] CELLULAR AND ANIMAL MODELS FOR DISEASES ASSOCIATED WITH MITOCHONDRIAL DEFECTS

[75] Inventors: Robert E. Davis, San Diego; Scott W. Miller, Solana Beach, both of Calif.

[73] Assignee: Mitokor, San Diego, Calif.

[21] Appl. No.: 397,808

[22] Filed: Mar. 3, 1995

Related U.S. Application Data

[63] Continuation-in-part of Ser. No. 219,842, Mar. 30, 1994, Pat. No. 5,565,323.
[51] Int. Cl.[6] .......................... A61K 48/00; A01N 63/00; C12P 21/04; C12N 15/00
[52] U.S. Cl. .................... 424/93.21; 424/93.3; 435/70.2; 435/172.2; 435/366
[58] Field of Search ............................... 424/93.21, 93.3; 435/69.1, 70.2, 172.2, 240.26, 346, 368, 366

[56] References Cited

PUBLICATIONS

Parker, Davis, *Ann. Neurol.* 26:719–723 (1989).
Jenner, P., *Acta Neurol. Scand.* 84:6–15 (1991).
Erlich, et al., "Specific DNA Amplification", *Nature* 331:461–462 (1988).
Richman, et al., "Human Immunodeficiency Virus Type 1 Mutants Resistant to Nonnucleotide Inhibitors of Reverse Transcriptase Arise in Tissue Culture", *Proc. Natl. Acad. Sci. USA* 88:11241–11245 (1991).
Wu and Wallace, "The Ligation Amplification Reaction (LAR)–amplification of Specific DNA Sequences Using Sequential Rounds of Template–dependent Ligation", *Genomics* 4:560–569 (1989).
Barany, et al., *PCR Methods and App.* 1:5–16 (1991).
Bowling, et al., "Age–Dependent Impairment of Mitochondrial Function in Primate Brain", *J. of Neurochemistry* 60(5):1964–1967 (1992).
Suggs, et al., "Use of Synthetic Oligonucleotides as Hybridization Probes: Isolation of Cloned cDNA Sequences for Human $\beta_2$–microglobulin", *Proc. Natl. Acad. Sci. USA* 78(11):6613–6617 (1981).
Saiki, et al., "Genetic Analysis of Amplified DNA with Immobilized Sequence–Specific Oligonucleotide Probes", *Proc. Natl. Acad. USA* 86:6230–6234 (1989).
Kuppuswamy, et al., "Single Nucleotide Primer Extension to Detect Genetic Diseases: Experimental Application to Hemophilia B (Factor IX) and Cystic Fibrosis Genes", *Proc. Natl. Acad. Sci. USA* 88:1143–1147 (1991).
Syvanen, et al., "A Primer–guided Nucleotide Incorporation Assay in The Genotyping of Apolipoprotein E" *Genomics* 8:684–692 (1990).
Landegren, et al., "A Ligase–mediated Gene Detection Technique", *Science* 241:1077–1080 (1988).
Conner, et al., "Detection of Sickle Cell $\beta^s$–globin Allele by Hybridization with Synthetic Oligonucleotides", *Proc. Natl. Acad. Sci. USA* 80:278–282 (1983).

Nickerson, et al., "Automated DNA Diagnostics Using An ELISA–based Oligonucleotide Ligation Assay", *Proc. Natl. Acad. Sci. USA* 87:8923–8927 (1990).
Fodor, et al., "Multiplexed Biochemical Assays with Biological Chips", *Nature* 364:555–556 (1993).
Fodor, et al., "Light–directed, Spatially Addressable Parallel Chemical Synthesis" *Science* 251: 767–773 (1991).
Matthews and Kricka, "Analytical Strategies for The Use of DNA Probes" *Analytical Biochemisty* 169:1–25 (1988).
Francis Barany, "Genetic Disease Detection and DNA Amplification Using Cloned Thermostable Ligase", *Proc. Natl. Acad. Sci. USA* 88:189–193 (1991).
Gibbs, et al., "Detection of Single DNA Base Differences by Competitive Oligonucleotide Priming", *Nucleic Acids Research* 2437–2448 (1989).
Ghosh, et al., "Use of Maleimide–thiol Coupling Chemistry for Efficient Syntheses of Oligonucleotide–enzyme Conjugate Hybridization Probes", *Bioconjugate Chem.* 1(1)71–76 (1990).
Ishii and Ghosh, "Bead–based Sandwich Hybridization Characteristics of Oligonucleotide–Alkaline Phosphatase Conjugates and Their Potential for Quantitating Target RNA Sequences", *Bioconjugate Chem.* 4(1):34–41 (1993).
Jablonski, et al., "Preparation of Oligodeoxynucleotide–alkaline Phosphatase Conjugates and Their Use as Hybridization Probes", *Nucleic Acids Research* 14(15):6115–6129 (1986).
Li, et al., "Enzyme–linked Synthetic Oligonucleotide Probes: Non–Radioactive Detection of Enterotoxigenic *Escherichia Coli* in Faecal Specimens", *Nucleic Acids Research* 15(13):5275–5287 (1987).
Newton, et al., "Analysis of Any Point Mutation in DNA. The Amplification Refractory Mutation System (ARMS)", *Nucleic Acids Research* 17(7):2503–2517 (1989).
Gingeras, et al., "Use of Self–sustained Sequence Replication Amplification Reaction to Analyze and Detect Mutations in Zidovudine–resistant Human Immunodeficiency Virus", *J. of Infectious Diseases* 164:1066–1074 (1991).

(List continued on next page.)

*Primary Examiner*—James Ketter
*Assistant Examiner*—William Sandals
*Attorney, Agent, or Firm*—Seed & Berry LLP

[57] ABSTRACT

Cybrid cell lines which have utility as model systems for the study of disorders that are associated with mitochondrial defects are described. The cybrids are constructed by treating immortal cell lines with an agent that irreversibly disables mitochondrial electron transport, and then transfecting the cells with mitochondria isolated from diseased tissue samples. Preferably, the immortal cell lines used are of an undifferentiated type that can be induced to differentiate, which results in the cybrids also being able to be induced to differentiate. One such cybrid was constructed using neuroblastoma cells and mitochondria from a patient suffering from Alzheimer's Disease. Methods for using such cybrids for screening drugs and therapies for utility in treating such disorders are also provided. In addition, cybrid animals, methods of producing them, and methods of using them in drug and therapy screening are also provided.

19 Claims, 5 Drawing Sheets

OTHER PUBLICATIONS

Parker et al., Neurology, 40:1302–03 (1990).
Anderson, et al. Nature 290: 457–465 (1981).
Bennett, et al., J. Geriat. Psych. Neurol., 5:93–101, (1992).
Kish, et al., J. Neurochem, 59: 776–779, (1992).
Chandrasekaran, et al., Brain Res., 606: 213–219, (1993).
Wallace, D. C., Science, 256: 628–632, (1992).
Wallace, et al., Epilepsia, 35(Supp. 1): 543–550, (1994).
Shoffner, et al., Genetics, 17: 171–184 (1993).
Simonian, et al., J. Neuropath. Exp. Neuro., 52: 580–585, (1993).
Partridge, et al., Arch. Biochem. Biophys., 310: 210–217, (1994).
Howell, et al., Hum. Genet., 49: 939–950, (1991).
Chandrasekaran, et al., J. Neurosci. Res., 32: 415–423, (1992).
Oberley, L.W., *J. Cell Physiol*, 138(1):50–60, Jan. 1989 (Abstract).
Peehl, D.M., *Carcinogenesis,* 18(8):1643–1650, Aug. 1997 (Abstract).
Gallimore, P.H., *Cell Growth Differ,* 8(7):763–771, Jul. 1997 (Abstract).
de Herreros, A.G., et al., *J. Biol Chem,* 264(33):19994–19999, Nov. 25 1989.
Miller et al. Creation and characterization of mitochondrial DNA–depleted cell lines with "neuronal–like" properties. J. Neurology vol. 67:1897–1907, Oct. 28, 1996.
Desjardins et. al. . . An established avian fibroblast cell line without mitochondrial DNA. Somat. Cell and Mol. Genet. . . vol. 12(2):133–139, Apr. 6, 1986.

Chomyn et. al. . . Platelet–mediated transformation of mtDNA–less human cells: Analysis of phenotypic variability among clones from normal individuals–and complemetation behavior or the tRNA–lys mutation causing myoclonic epilepsy and ragged red fibers. A, Jun. 2, 1994.

Yoneda et. al. . . Marked replicative advantage of human mtDNA carrying a point mutation that causes the MELAS encephalomyopathy. PNAS (USA) vol. 89:11164–11168, Dec. 1992.

Morais. Isoaltin of avian mitochondrial DNA–less cells. Methods in Enzymology, vol. 264:296–304, Jun. 1996.

King and Attardi. Isolation of human cell lines lacking mitochondrial DNA. Mehtods in Enzymology. vol. 264:304–334, Jun. 1996.

Zinnkewich–Peotti et. al. . . Mitochondrial DNA modulation of the anchorage–independent phenotype of transformed avian cells. Cancer Res. vol. 50:6675–6682, Oct. 15, 1990.

King and Attardi. Science. vol. 246:500–503, Oct. 27, 1989.

King et. al. . . Mol. and Cell Biol. . . vol. 12(2):480–490, Feb. 15, 1992.

Herzberg et. al. . . Bioch. Biophys. Acta. vol. 1181:63–67, Feb. 25, 1993.

Shoffner, et. al. . . Genomics. vol. 17:171–184, Jul. 22, 1993.

Hawkins et. al. . . Life Sci. . . vol. 28(4):425–432, May 5, 1981.

CELLULAR AND ANIMAL MODELS FOR DISEASES ASSOCIATED WITH MITOCHONDRIAL DEFECTS

This application is a continuation-in-part of co-pending application Ser. No. 08/219,842 filed on Mar. 30, 1994 now U.S. Pat. No. 5,565,323, which is incorporated herein by reference.

FIELD OF THE INVENTION

The present invention relates generally to model systems for diseases that involve defects in the function of mitochondria, where those defects arise from defects in the genes of those mitochondria. The invention also relates to the use of these model systems for screening drugs and evaluating the efficacy of treatments for those diseases. It also relates to the use of these model systems for the diagnosis of such diseases.

BACKGROUND OF THE INVENTION

A number of degenerative diseases are thought to be caused by or be associated with alterations in mitochondrial metabolism. These include Alzheimer's Disease, Parkinson's Disease, Huntington's disease, dystonia, Leber's hereditary optic neuropathy, schizophrenia, and myodegenerative disorders such as "mitochondrial encephalopathy, lactic acidosis, and stroke" (MELAS), and "myoclonic epilepsy ragged red fiber syndrome" (MERRF).

Alzheimer's disease (AD) is a progressive neurodegenerative disorder that is characterized by loss and/or atrophy of neurons in discrete regions of the brain, and that is accompanied by extracellular deposits of β-amyloid and the intracellular accumulation of neurofibrillary tangles. It is a uniquely human disease, affecting over 13 million people worldwide. It is also a uniquely tragic disease. Many individuals who have lived normal, productive lives are slowly stricken with AD as they grow older, and the disease gradually robs them of their memory and other mental faculties. Eventually, they cease to recognize family and loved ones, and they often require continuous care until their eventual death.

Individuals who are afflicted with AD may have one of two forms of this disease: "familial" AD or "sporadic" AD. Familial AD has an early onset, usually beginning in the forties or fifties. As the name suggests, the occurrence of this form of AD follows conventional patterns of Mendelian inheritance. Sporadic AD, which is believed to account for 90–95% of all cases of AD, is a late-onset disease which is not inherited in Mendelian fashion, and it thus does not appear to be caused by nuclear chromosomal abnormalities.

There is evidence that defects in oxidative phosphorylation are at least a partial cause of sporadic AD. The enzyme cytochrome C oxidase (COX), which makes up part of the mitochondrial electron transport chain (ETC), is present in normal amounts in AD patients; however, the catalytic activity of the enzyme in AD patients and in the brains of AD patients at autopsy has been found to be abnormally low. This suggests that the genes for COX in AD patients are defective, leading to decreased catalytic activity that in some fashion causes or contributes to the symptoms that are characteristic of AD.

COX in humans and other mammals, is composed of at least 13 subunits. At least ten of these subunits are encoded by nuclear genes; the remaining three subunits (COX I, II and III) are encoded by mitochondrial genes. The catalytic centers of COX are associated with COX I and COX II. Thus, catalysis by COX is dependent upon the proper function of two of the subunits that are encoded for by the mitochondrial DNA (mtDNA).

Specific point mutations in the mtDNA genes that encode for COX subunits I and II segregate with AD, and are rarely found in age-matched controls or patients with other neurological disorders. These specific AD-associated mtDNA point mutations result in alterations in the primary structure of the encoded proteins, and these might be expected to perturb COX catalytic activity by distorting the secondary and/or tertiary structures of the COX complex. The reduced COX activity caused by these defects could lead to increased intracellular levels of oxygen free radicals; and the cumulative effects of free radical-mediated lipid oxidation ultimately cause the degenerative neurological changes that are characteristic of AD (1).

Parkinson's disease (PD) is a progressive neurodegenerative disorder characterized by the loss and/or atrophy of dopamine-containing neurons in the pars compacta of the substantia nigra of the brain. Like AD, PD also afflicts the elderly. It is characterized by bradykinesia (slow movement), rigidity and a resting tremor. Although L-Dopa treatment reduces tremors in most patients for a while, ultimately the tremors become more and more uncontrollable, making it difficult or impossible for patients to even feed themselves or meet their own basic hygiene needs.

Like sporadic AD, most cases of PD appear sporadically in the population; even with identical twins, one may have the disease, and the other not. This suggests that nuclear chromosomal abnormalities are not the cause of this disease. Furthermore, it has been shown that the neurotoxin 1-methyl-4-phenyl-1,2,3,6-tetrahydropyridine (MPTP) induces parkinsonism in animals and man. MPTP is converted to its active metabolite, MPP+, in dopamine neurons; it then becomes concentrated in the mitochondria. The MPP+ then selectively inhibits the enzyme NADH:UBIQUINONE OXIDOREDUCTASE ("Complex I"), leading to the increased production of free radicals, reduced production of adenosine triphosphate, and ultimately, the death of affected dopamine neurons.

Complex I is composed of 40–50 subunits; most are encoded by the nuclear genome and seven by the mitochondrial genome. Since parkinsonism may be induced by exposure to mitochondrial toxins that affect Complex I activity, it appears likely that defects in the mitochondrial genes that encode Complex I proteins may contribute to the pathogenesis of PD by causing a similar biochemical deficiency in Complex I activity. Indeed, defects in mitochondrial Complex I activity have been reported in the blood and brain of PD patients (2).

Similar theories have been advanced for similar relationships between mtDNA mutations and other neurological diseases, including Leber's hereditary optic neuropathy, schizophrenia, "mitochondrial encephalopathy, lactic acidosis, and stroke" (MELAS), and "myoclonic epilepsy ragged red fiber syndrome" (MERRF).

The identification of therapeutic regimens or drugs that are useful in the treatment of disorders associated with such mitochondrial defects has historically been hampered by the lack of reliable model systems that could be used in rapid and informative screening. Animal models do not exist for many of the human diseases that are associated with mitochondrial gene defects. In addition, appropriate cell culture model systems are either not available, or are difficult to establish and maintain. Furthermore, even when cell culture models are available, it is often not possible to discern whether the mitochondrial or the cellular genome is responsible for given phenotype, as mitochondrial functions are often encoded by both genomic and mitochondrial genes. It is therefore also not possible to tell whether the apparent effect of a given drug or treatment operates at the level of the mitochondrial genome or elsewhere.

One approach that has been used to attempt to discern which genome is responsible is to destroy the mitochondrial DNA in cultured cells known to have proper mitochondrial function, and then transfer to such cells the mitochondria from diseased cells (3). However, the resulting cell lines tend to be unstable and hard to culture. Fully differentiated cell lines are used as the targets for transplantation, but their naturally limited life spans makes them particularly unsuitable for screening purposes. In addition, such transformations have not been done using cells of the type that are most affected by the disease, making it unclear whether the mitochondrial deficiencies observed in the transformants are related to the disease state being studied.

ADVANTAGES AND SUMMARY OF THE INVENTION

The present invention provides model systems for diseases that are associated with or caused by defects in mitochondrial metabolism. It also provides methods for the use of these model systems for screening and evaluating drugs and treatments for such disorders. In addition, it provides methods for using these model systems to diagnose such disorders.

The primary advance offered by the present invention is that it for the first time offers stable cultures of cells that have had their mitochondria transplanted from other cells. Published studies have reported transplanting mitochondria into fully differentiated (mature) cells, but these cells are not maintainable, and eventually the cultures die. In contrast, the present invention teaches that if mitochondria are transplanted into an immortal, differentiatable cell line, the transplanted cells are also immortal. It further teaches the induction of differentiation among a subpopulation of the immortal culture, which allows for the same experiments to be done as would otherwise have been possible had the transplant been made directly into the differentiated cells.

Another advance of the present invention is that it offers model systems that have greater relevance to the disorder under study. Published articles used osteosarcoma (bone cancer) cells as the recipients of transplanted mitochondria; however, bone cells are not a primary site of pathogenesis for the neurological diseases for which those transformants were offered. The present invention contemplates that the immortalized target cells for mitochondrial transplant would be selected such that they would be capable of differentiation into cells of the type that are primarily affected in the disease state under study. For example, in the examples herein, mitochondria from an AD patient are transplanted into neuroblastoma cells, subcultures of which can be induced to differentiate into neurons. The phenotypic expression of the mitochondrial defects in this model system can thus be observed in the very cell type that is most affected by the disease.

The present invention also provides for the transplantation of mitochondria into undifferentiated germ cells or embryonic cells, thus providing for the maturation of test animals having mitochondria that have been wholly or partially derived from cells of a diseased organism.

The model systems that are within the scope of the present invention offer outstanding opportunities to identify, probe and characterize defective mitochondrial genes and mutations thereof, to determine their cellular and metabolic phenotypes, and to assess the effects of various drugs and treatment regimens. For example, in one embodiment, mitochondria from cells of an AD patient are transferred to neuroblastoma cells. These are maintained in culture, and, when desired, chemically induced to differentiate into cells with a "neuronal-like" phenotype. The differentiated cells undergo phenotypic changes characteristic of AD; for example, reduced activity of cytochrome C oxidase (COX). If exogenous agents or treatments are used on such samples and are able to prevent, delay, or attenuate the phenotypic change, then those agents or treatments warrant further study for their ability to prevent, delay or attenuate AD in humans.

Because such cell systems are observed to undergo phenotypic changes characteristic of the diseases to which they relate, they can also be used as methods of diagnosis. For example, cells can be taken from an individual presenting with behavioral symptoms of AD, and the mitochondria from those cells can be put into neuroblastoma cells, and samples of these cultures can then be chemically induced to differentiate into neuron-like cells. If the differentiated cells that contain the patient's mitochondria begin to exhibit the degenerative phenotype that is characteristic of AD, this confirms that the mitochondria carry one or more causative mtDNA mutation. It thus confirms the diagnosis of AD.

By using these same cultures in screening, it is also possible to predict which of several possible drugs or therapies may be best for that particular patient.

It is therefore an object of the present invention to provide an immortal $\rho°$ cell line.

It is another object of the present invention to provide an immortal $\rho°$ cell line that is undifferentiated, but is capable of being induced to differentiate.

It is a further object of the present invention to provide a cybrid cell line, comprising cultured immortal cells having genomic and mitochondrial DNAs of differing biological origins.

It also is an object of the present invention to provide a cybrid cell line, comprising cultured immortal cells having genomic DNA with origins in a neuroblastoma cell line, and mitochondrial DNA having its origin in a human tissue sample derived from an individual with a disorder known to be associated with a mitochondrial defect.

It is also an object of the present invention to provide model systems for the study of disorders which are associated with mitochondrial defects.

It is another object of the invention to provide model systems for the screening of drugs effective in treating disorders associated with mitochondrial defects.

A further object of the present invention is to provide model systems for the evaluation of therapies for effectiveness in treating disorders associated with mitochondrial defects.

Another object of the invention is to provide model systems for the diagnosis of disorders associated with mitochondrial defects.

It is a further object to provide methods for the construction of the above-mentioned model systems.

An additional object is to provide methods for using these model systems for drug screening, therapy evaluation, and diagnosis.

It is a further object of the present invention to provide animal models for diseases that are associated with mitochondrial defects. These animals models are useful for drug screening, therapy evaluation and diagnosis.

A further object of the present invention is to provide methods of making such animal models.

These and further objects of the invention will become more apparent by the more detailed description of the invention provided herein below.

DETAILED DESCRIPTION OF THE INVENTION

Methods for depleting mitochondrial DNA ("mtDNA") from cells and then transforming those cells with mitochondria from other cells have been reported in the literature. King and Attardi (4) created human cells lacking mtDNA ($\rho^\circ 206$ –143B human osteosarcoma cells) and then repopulated these cells with mitochondria from foreign cells. Transformants with various mitochondrial donors exhibited respiratory phenotypes distinct from the host and recipient cells, indicating that the genotypes of the mitochondrial and nuclear genomes, or their interaction, play a role in the respiratory competence of cells. Chomyn et al. (5) repopulated $\rho^\circ 206$ cells with mitochondria derived from myoblasts of patients carrying MELAS-causing mutations in the mitochondrial gene for tRNA$^{leu}$. The transformed cells were deficient in protein synthesis and respiration, mimicking muscle-biopsy cells from MELAS patients. More recently, Chomyn et al. (3) reported the use of blood platelets as a source of mitochondrial donors for repopulation of $\rho^\circ$ cells.

However, the techniques for mitochondrial transformation of human cells described above allow only limited short term studies. Care has to be taken in growing cultures since transformed, undifferentiated cells containing wild-type mtDNA are healthier than those containing mutant mtDNA and therefore have a propagative advantage in culture. Over the course of several generations, cells with wild-type mtDNA would dominate the cellular population (i.e., mutant mtDNA would be selected against) and cells containing mutated mtDNA would be lost.

In addition, the value of the previous cell lines is further limited because they are not of the same type as those cells in which pathogenesis of the disease is expressed. For example, Chomyn (3) used osteosarcoma cells as the recipient of mitochondria from cells of a MERRF patient. Yet the major impact of MERRF on patients is that it affects the brain and muscle to cause encephalomyopathy and myopathy. There is no known pathogenesis in bone cells.

The present invention overcomes these two serious limitations. First, by introducing mitochondria from diseased cells into an undifferentiated, immortal cell line, it is possible to maintain the transformants in culture almost indefinitely. Although it would be possible to study and use the undifferentiated cells themselves, it is preferred to take a sample of such cells, and then induce them to differentiate into the cell type that they are destined to become. For example, for neurodegenerative disease, cultures of primary neurons or neuroblastoma cell lines are preferred because these can be terminally differentiated after transfer of mtDNA with phorbol esters, growth factors and retinoic acid. Transfer of mtDNA into these cells results in cells that carry mutant mitochondrial mtDNA and which differentiate into post-mitotic cells with a neuronal or neuronal-like phenotype.

Post-mitotic cells with a neuronal phenotype have several advantages over other cells. Obviously, these cells are closer to the phenotype of cells affected in neurodegenerative disease. Since these cells are not actively dividing, the propagative advantage of cells containing wild-type mtDNA is not a significant problem during the test period (i.e., cells containing mutant mtDNA are not selected against in tissue cultures). Also, when terminally differentiated, these cells are stable in culture. Post-mitotic cells accumulate mutant mtDNA over their life span in culture, resulting in enhanced bioenergetic failure with increasing time in culture. This leads to an exacerbation of mitochondrial dysfunction and alterations in biochemical events consistent with bioenergetic failure.

Thus, using $\rho^\circ$ cells derived from cultures of primary neurons or neuroblastoma cell lines permits analysis of changes in the mitochondrial genome and closely mimics the functional effects of mitochondrial dysfunction in neurons and cells.

Mitochondria to be transferred to construct model systems in accordance with the present invention can be isolated from virtually any tissue or cell source. Cell cultures of all types could potentially be used, as could cells from any tissue. However, fibroblasts, brain tissue, myoblasts and platelets are preferred sources of donor mitochondria. Platelets are the most preferred, in part because of their ready abundance, and their lack of nuclear DNA. This preference is not meant to constitute a limitation on the range of cell types that may be used as donor sources.

Recipient cells useful to construct models in accordance with the present invention are undifferentiated cells of any type, but immortalized cell lines, particularly cancerous cell lines, are preferred, because of their growth characteristics. Many such cell lines are commercially available, and new ones can be isolated and rendered immortal by methods that are well known in the art. Although cultured cell lines are preferred, it is also possible that cells from another individual, e.g., an unaffected close blood relative, are useful; this could have certain advantages in ruling out non-mitochondrial effects. In any event, it is most preferred to use recipient cells that can be induced to differentiate by the addition of particular chemical (e.g., hormones, growth factors, etc.) or physical (e.g., temperature, exposure to radiation such as U.V. radiation, etc.) induction signals.

It is most preferred that the recipient cells be selected such that they are of (or capable of being induced to become) the type that is most phenotypically affected in diseased individuals. For example, for constructing models for neurological diseases that are associated with mitochondrial defects, neuronal or neuroblastoma cell lines are most preferred.

In the examples below, mitochondria have been isolated by an adaptation of the method of Chomyn (3). However, it is not necessary that this particular method be used. Other methods, are easily substituted. The only requirement is that the mitochondria be substantially purified from the source cells and that the source cells be sufficiently disrupted that there is little likelihood that the source cells will grow and proliferate in the culture vessels to which the mitochondria are added for transformation.

In the examples, the mitochondrial DNA (mtDNA) of the target cells is removed by treatment with ethidium bromide. Presumably, this works by interfering with transcription or replication of the mitochondrial genome, and/or by interfering with MRNA translation. The mitochondria are thus rendered unable to replicate and/or produce proteins required for electron transport, and the mitochondria shut down, apparently permanently. However, it is important to note that it is not necessary for the purposes of this invention to use any particular method to remove the mitochondria or mitochondrial DNA.

Model systems made and used according to the present invention irrespective of whether the disease of interest is known to be caused by mitochondrial disorders are equally useful where mitochondrial defects are a symptom of the disease, are associated with a predisposition to the disease, or have an unknown relationship to the disease. In addition, the use of model systems according to the present invention to determine whether a disease has an associated mitochondrial defect are within the scope of the present invention.

In addition, although the present invention is directed primarily towards model systems for diseases in which the mitochondria have metabolic defects, it is not so limited. Conceivably there are disorders wherein there are structural or morphological defects or anomalies, and the model systems of the present invention are of value, for example, to find drugs that can address that particular aspect of the disease. In addition, there are certain individuals that have or are suspected of having extraordinarily effective or efficient mitochondrial function, and the model systems of the present invention may be of value in studying such mitochondria. In addition, it may be desirable to put known normal mitochondria into cell lines having disease characteristics, in order to rule out the possibility that mitochondrial defects contribute to pathogenesis. All of these and similar uses are within the scope of the present invention, and the use of the phrase "mitochondrial defect" herein should not be construed to exclude such embodiments.

It is important to an understanding of the present invention to note that all technical and scientific terms used herein, unless otherwise defined, are intended to have the same meaning as commonly understood by one of ordinary skill in the art. The techniques employed herein are also those that are known to one of ordinary skill in the art, unless stated otherwise.

The terms used herein are not intended to be limiting of the invention. For example, the term "gene" includes cDNAs, RNA, or other oligonucleotides that encode gene products. The term "tissue" includes blood and/or cells isolated or suspended from solid body mass, as well as the solid body mass of the various organs. In addition, "expression" of a gene or nucleic acid encompasses not only cellular gene expression, but also the transcription and translation of nucleic acid(s) in cloning systems and in any other context. "Immortal" cell lines denotes cell lines that are so denoted by persons of ordinary skill, or are capable of being passaged preferably an indefinite number of times, but not less than ten times, without significant phenotypical alteration. "$\rho^\circ$ cells" are cells essentially depleted of functional mitochondria and/or mitochondrial DNA, by any method useful for this purpose.

Reference to particular buffers, media, reagents, cells, culture conditions and the like, or to some subclass of same, is not intended to be limiting, but should be read to include all such related materials that one of ordinary skill in the art would recognize as being of interest or value in the particular context in which that discussion is presented. For example, it is often possible to substitute one buffer system or culture medium for another, such that a different but known way is used to achieve the same goals as those to which the use of a suggested method, material or composition is directed.

Although the cells used in one embodiment herein are neuroblastoma cells, the present invention is not limited to the use of such cells. Cells from different species (human, mouse, etc.) or different tissues (breast epithelium, colon, neuronal tissue, lymphocytes, etc.) are also useful in the present invention.

The disclosures of the publications listed in the bibliography are hereby incorporated by reference in this application, in order to more fully describe the state of the art to which this invention pertains.

The following examples are provided, not to limit the present invention, but to illustrate it.

EXAMPLES

Materials and Methods

Reagents. Cell culture media were purchased from Gibco BRL (Gaithersburg, Md.). 5,5',6,6'-tetrachloro-1,1',3,3'-tetraethylbenzimidazolo-carbocyanine iodide (JC-1) and nonyl acridine orange were obtained from Molecular Bioprobes (Eugene, Oreg.). Unless otherwise indicated, all other reagents were from Sigma Chemical Co. (St. Louis, Mo.).

Cell Culture. SH-SY5Y neuroblastoma cells (6) were grown in Dulbecco's modified Eagle's medium (DMEM) supplemented with 10% heat-inactivated fetal bovine serum (FBS), penicillin (100 IU/ml), streptomycin (50 $\mu$g/ml), glucose (4500 mg/ml), 25 mM HEPES, and glutamine (584 mg/ml) at 37° C. in 5% $CO_2$. In order to heat inactivate the FBS, it was thawed overnight at 4° C., warmed to 37° C., then heated to 56° C. for 30 minutes. DMEM was chosen over RPMI 1640 medium since RPMI is known to inhibit production of mitochondrial DNA (mtDNA) in depleted ($\rho^\circ$) cell lines (7).

Oxygen Consumption Measurements. Cells were trypsinized from a 75 $cm^2$ flask, rinsed one time with HBSS (Hanks Balanced Salt Solution, Gibco BRL), resuspended at $2.0 \times 10^7$ cell/ml in HBSS, and maintained at 37° C. An 80 $\mu$l cell suspension sample was introduced into a Haas stirred polarographic microchamber (8) in a final volume of 330 $\mu$l in HBSS. Oxygen consumption was measured by a Yellow Springs Clark oxygen electrode No. 5531 and monitor No. 5300 (Yellow Springs, Ohio) at 37° C. Oxygen utilization was calculated as described by Estabrook (9).

Enzymatic Assays and Protein Determinations.

Citrate synthase activity was determined using samples of $2 \times 10^5$ cells incubated at 30° C. in a cuvette containing 0.04% triton X-100, 0.1 mM 5,5'-dithio-bis(2-nitrobenzoic) acid, 980 µl of 100 mM tris pH 8.0 for 3 minutes prior to the assay. To initiate the reaction, 10 µl of acetyl CoA and oxaloacetic acid to final concentrations of 50 µM and 500 µM, respectively, were added. The cuvette was mixed by inversion and the increase in absorbance at 412 nm was recorded for 2 to 3 minutes. The reaction is linear over this time period (10).

Complex IV (cytochrome c oxidase) and complex II (succinic dehydrogenase) activities were determined essentially as described (11,12) except that cells ($6 \times 10^5$ cells for COX activity and $2 \times 10^5$ cells for succinic dehydrogenase) rather than isolated mitochondria were assayed, and membranes were lysed by incubation with n-dodecyl-beta-D-maltoside (0.2 mg/ml) for three minutes at 30° C. prior to measurement of enzymatic rates. The assay reaction was initiated by the addition of reduced cytochrome c to the cuvette, which was inverted twice. The change in absorbance at 550 nm was measured continuously for 90 seconds. The fu y oxidized absorbance value was determined by the addition of a few grains of ferricyanide to the cuvette. Rates were obtained at various cell concentrations to validate that the assay was in a linear range. Non-enzymatic background activity was determined by pre-incubation of the cells with 1 mM potassium cyanide (KCN) prior to determination of the rate constant. Cyanide sensitive complex IV activity was calculated as a first-order rate constant after subtraction of background activity. Complex II activity was assayed by adding the cells to a cuvette containing assay buffer (10 mM succinate, 35 mM potassium phosphate, pH 7.2, 200 µg/ml n-dodecyl-beta-D-maltoside, 1 mM KCN, 5 mM $MgCl_2$, 1 µM rotenone and 1 µM antimycin A). Assay volume was adjusted to a volume of 887 with assay buffer. After incubation at 30° C. for 10 minutes, 100 µl of 0.6 mM 2,6-dichorophenolindophenol (DCIP), as the final electron acceptor, was added for one minute for temperature equilibration. Three µl of a 20 mM solution of the synthetic ubiquinone analog, Q1 (Intermediate electron acceptor), was added to initiate the reduction of DCIP. The change in absorbance at 600 nm for 1–3 minutes at 30° C. was determined. Rates were obtained at various cell concentrations to validate that the assay was in a linear range. Background was determined by a repeat reaction in the presence of 10 mM malonate (competitive inhibitor). Specific complex II activity was calculated by subtracting malonate-inhibited background. All enzymatic activities were normalized to total cellular protein as determined by the Lowry method (13).

Complex I (NADH:ubiquinone oxidoreductase) activities were determined essentially as described previously (2) except that cells rather than isolated mitochondria were assayed. Membranes were lysed by incubation of cells at $2 \times 10^6$ cells/ml with 0.005% digitonin in Hank's buffered salts plus 5 mM EDTA (HBSS/EDTA) for 20 seconds at 23° C. The solubilization was stopped by addition of 50 volumes of cold HBSS/EDTA. The lysed cells were centrifuged at 14,000 g for 10 minutes at 4° C. The pellet was diluted to approximately 1 mg/ml protein in HBSS/EDTA with 1 µM leupeptin, 1 µM pepstatin and 100 µM PMSF. Prior to complex I assays a 200 µl aliquot of protein suspension in a 1.5 ml eppendorf tube was sonicated for 6 minutes in an ice packed cup horn sonicator (Heat Systems-Ultrasonics model W225) at 50% duty cycle. The complex I assay reaction was initiated by the addition of 3 µl of 20 mM ubiquinone-1 in ethanol to 10 µl of 10 mM NADH (in assay buffer), and 30–100 µg of protein in a 1 ml total volume of assay buffer (25 mM potassium phosphate, pH 8.0, 0.25 mM EDTA, and 1.5 mM potassium cyanide) in a 1 ml cuvette that had been pre-incubated at 30° C. for 3 minutes. The change in absorbance at 340 nm was measured for 120 seconds after which 5 µl of 500 µM rotenone in ethanol was added and the absorbance change was measured for another 120 seconds, to determine the rotenone sensitive Complex I activity. Complex I activity was defined as the total rate (without rotenone)–total rate (with rotenone). The rates are calculated from the maximum linear portion of the curve using 6.81 $mM^{-1}$ as the combined NADH-Q1 extinction coefficient at 340 nm.

Dye Uptake. Cells were plated in 96 well microplates at $4-50 \times 10^3$ cells/well overnight. Medium was decanted and the cells rinsed once with HBSS. The cells were incubated with 5,5',6,6'-tetrachloro-1,1',3,3'-tetraethylbenzimidazolo-carbocyanine iodide (JC-1, 16 µM) or nonyl acridine orange (1 µg/ml) for sixty minutes at 37° C., with $CO_2$, in a 100 nanoliter volume of HBSS. The medium was decanted and the cells rinsed three times with 200 µl of HBSS and left in 100 µl HBSS. Dye uptake was measured using a Millipore CYTOFLUOR No. 2350 fluorescence measurement system (Bedford, Mass.). Filter sets used for JC-1 and nonyl acridine orange were 485 nm (excitation) and 530 nm (emission). Bandwidths for the 485 nm, and 530 nm filters were 20 nm, and 25 nm respectively. Dye uptake by the cells was optimized for incubation time, concentration, and cell number, and shown to be linear with respect to cell number under the conditions chosen (manuscript in preparation). To define non-specific uptake of the mitochondrial membrane potential sensitive dye (JC-1), carbonyl cyanide m-chlorophenyl hydrazone (CCCP, 5 µM) was added concurrently with JC-1 to uncouple electron transport and dissipate the mitochondrial membrane potential (20).

In some experiments, dye uptake was also quantitated by fluorescence activated cell sorting (FACS-SCAN, Becton-Dickinson) using dye concentrations and incubation times described above. Growing cells were trypsinized from a 75 $cm^2$ flask, rinsed one time with PBS+1 mg/ml glucose, resuspended in the same buffer, split into separate tubes, treated and incubated with dye. After incubation, the cells were centrifuged at 200×g for 10 minutes, the incubation medium was decanted, and the stained cells were resuspended in 2 ml of PBS+1 mg/ml glucose and the cells were held on ice prior to FACS analysis. FACS analysis was carried out on $1 \times 10^4$ cells with an excitation filter of 485 nm and an emission filter of 530 nm and a bandwidth of 42 nm. Slot blot analysis of mtDNA. Total DNA from $10^7$ SH-SYSY parental and $\rho^\circ$ cell isolates was isolated by a Qiagen Kit (Chatsworth, Calif.) and quantitated by absorbance at 260 nm and by agarose gel electrophoresis. Various amounts of total DNA were de natured by treatment with 0.2N NaOH in 100 µl volume at 65° C. for 30 minutes. The sample was neutralized with 100 µl of 2M $NH_4OAC$. The DNA was vacuum blotted onto a ZETA PROBE membrane (Bio-Rad, Richmond, Calif.), and was wetted with 10× SSC (1.89M sodium chloride, 188 mM sodium citrate, pH 7.0). The membrane was then exposed to UV light (254 nm, 125 mJoule) and incubated with blocking buffer (0.2% I-Block, 0.5× SSC, 0.1% Tween-20) for 30 minutes at ambient temperature. The membrane was washed with hybridization buffer (5× SSC, 1% SDS, 0.5% BSA) in an open small volume plastic dish.

Alkaline phosphatase-oligo conjugates were prepared as described by Ghosh (14). Ten mls of hybridization buffer containing 2 pmol/ml of AP-oligo conjugate against the COX I subunit, specific for human mtDNA (CGTTTGGTATTGGGTTATGGC) (SEQ ID NO 1), was layered on the membrane and incubated for 60 minutes at 42° C. The membrane was washed three times with buffer 1 (1× SSC, 0.1% SDS, 5 minutes at RT), one time with buffer 2 (0.5× SSC, 0.1% SDS, three minutes at 50° C.), one time with buffer 3 (1× SSC, 1% triton X-100, three minutes at RT), one time with buffer 4 (1× SSC for ten minutes at RT) and finally one time briefly with development buffer (50 mM NaHCO$_3$, 1 mM MgCl$_2$, pH 9.5). The membrane was developed with LUMI-PHOS (Boehringer Mannheim, Indianapolis, Ind.) as per manufactures procedures. To quantitate the mtDNA a standard curve of known quantities of plasmid containing the COX I gene was blotted at the same time.

Example 1
Preparation of Immortalized ρ° Cell Lines

In order to produce cell lines expressing mitochondrial-DNA mutations that could be propagated and maintained in an undifferentiated state, and which could then undergo terminal differentiation, neuroblastoma cells were depleted of mitochondrial DNA, and mitochondria isolated from platelets of an AD patient were placed into those cells.

In order to convert them into ρ° cells, SH-SY5Y neuroblastoma cells (6) were cultured in the presence of ethidium bromide for varying periods of time (30–70 days) and at varying concentrations (0.01 to 5 pg/ml). The cells were passaged every week, and the media was changed every 3 days. Ethidium bromide concentrations higher than these resulted in cell death after 2 to 3 weeks. A noticeable fall off in growth rate occurred at approximately 33 days. Cell lines chosen for further study were exposed to the various concentrations for either 33 or 64 days. Cell lines treated for 33 days, 45 days or 64 days 5.0 μg/ml ethidium bromide (EtBr) were designated ρ° 33/5, ρ° 45/5 and ρ° 64/5, respectively.

Figure 1:
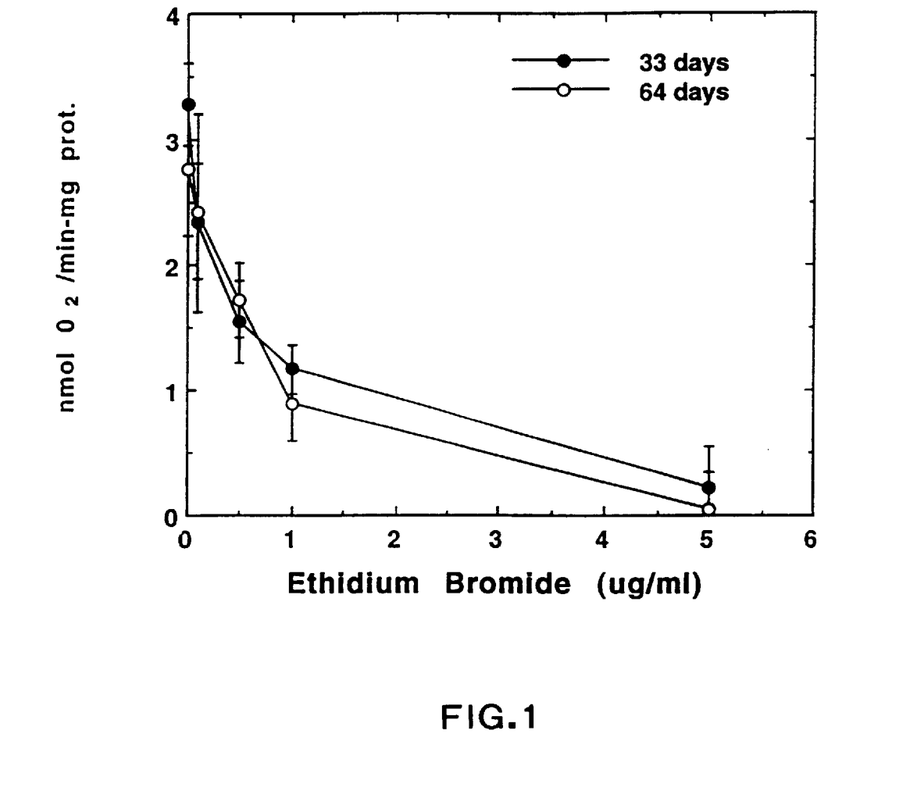
FIG. 1 is a graph showing that cyanide-sensitive oxygen consumption decreases with ethidium bromide treatment, indicating that endogenous mitochondrial oxidative phosphorylation has been disabled.

Production of respiration deficient mutants was monitored by cyanide inhibitable O$_2$ utilization. It was observed that oxygen utilization declined as a function of time and ethidium bromide concentration and was undetectable after 64 days of exposure to 5.0 μg/ml concentration of ethidium bromide, as shown in FIG. 1 (see also Table I). Oxygen utilization was determined polarographically in cells treated for either 33 days (closed circles) or 64 days (open circles) with varying concentrations of EtBr. Nonspecific O$_2$ consumption was determined in the presence of 1 mM KCN and was subtracted from measured total rates. Data are shown S.E.M. for at least 2 independent experiments.

Figure 2:
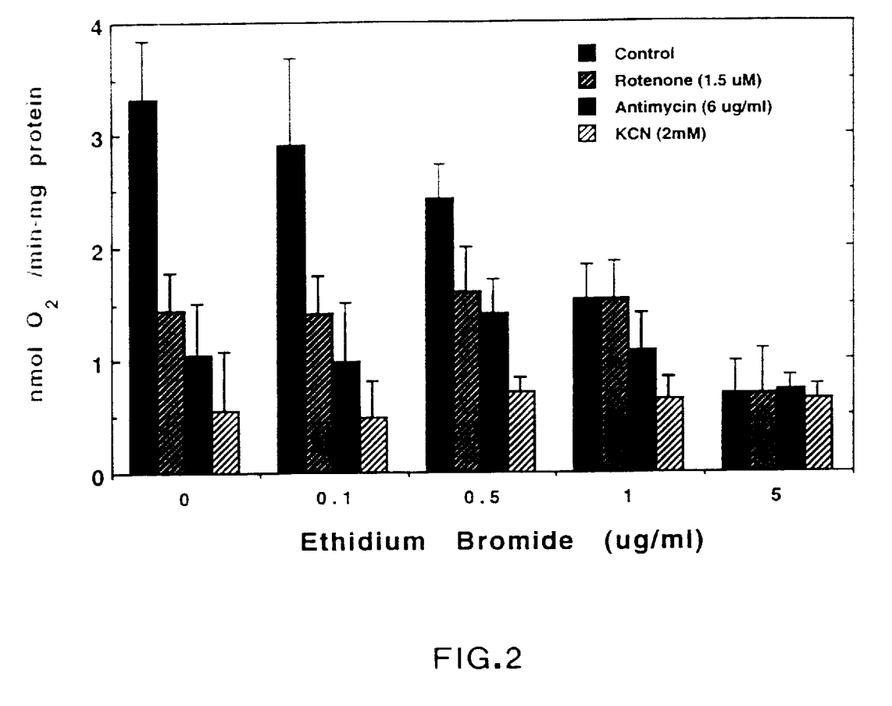
FIG. 2 is a graph showing that ethidium bromide treatment diminishes the sensitivity of cellular oxygen uptake to various electron transport chain inhibitors, confirming that ethidium bromide has disabled the endogenous electron transport chain.

The effectiveness of ethidium bromide in shutting down electron transport was confirmed by treating cells for 64 days with EtBr at various concentrations, and then measuring oxygen consumption in the presence of specific inhibitors of complex I (rotenone), complex III (antimycin), and complex IV (cyanide). As shown in FIG. 2, treatment with ethidium bromide at 5 μg/ml resulted in suppression of virtually all oxygen utilization that was sensitive to either complex I inhibition or complex III inhibition (FIG. 2). Data are shown S.E.M. for at least 2 independent experiments.

Figure 3:
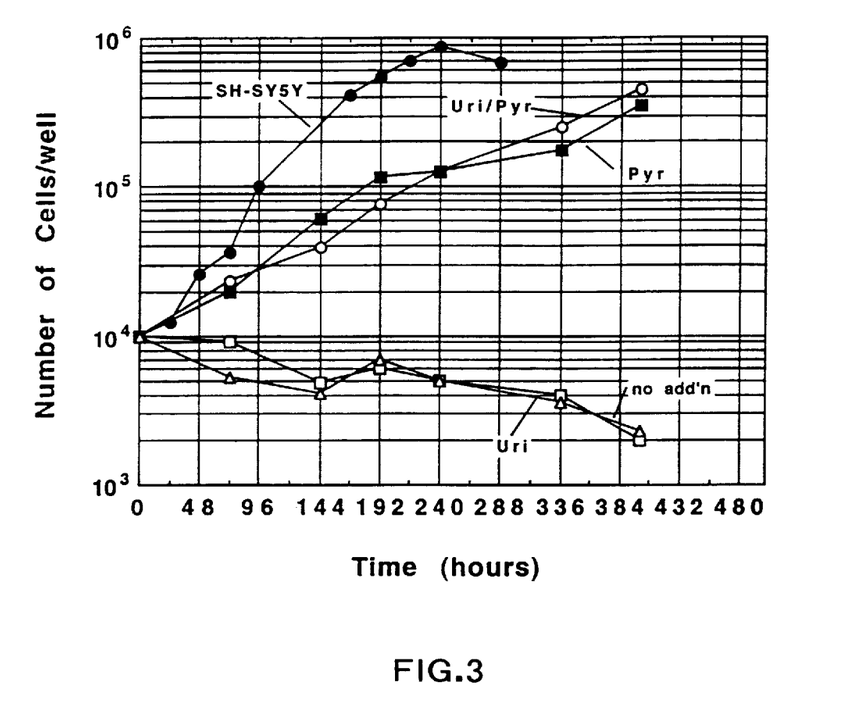
FIG. 3 is a graph showing that $\rho^\circ$ cells of the present invention are dependent on pyruvate, but not uridine, for growth.

Complex II enzyme activity was less perturbed, since none of its subunits are encoded by mitochondrial DNA, and its proteins are apparently normally transported and inserted into the enlarged mitochondria of ρ° cells in a functional state. Similarly, activity of the mitochondrial matrix enzyme citrate synthase, was comparable in parental and ρ° SH-SY5Y cells, but decreased by approximately 50% in ρ° 64/5 cells. The unresponsiveness of this enzyme is not surprising since it is encoded by nuclear genes, and its expression should not be affected by mtDNA depletion. It apparently is also normally transported and inserted into the enlarged mitochondria of ρ° cells in a functional state. These findings are confirmed by direct measurement of the activities of complex IV, Complex II, and citrate synthetase (Table I); note that complex IV activity for both the ρ° 64/5 cells and ρ° 33/5 cells were virtually undetectable.

ρ° cells were cultured in SH-SY5Y medium supplemented with uridine (50 μg/ml) and pyruvate (100 μg/ml) in order to support growth (4,15). As shown in FIG. 3, ρ° 64 days/5 μg/ml ethidium bromide ("ρ° 64/5") propagated in the presence of 100 μg/ml pyruvate (closed squares) or both pyruvate and uridine (open circles) thrived, but ρ° 64/5 cells placed in media containing 50 μg/ml uridine (open squares) or no addition (open triangles) did not. Parental SH-SYSY (solid circles) were grown as a positive control with no addition (solid circles), and not surprisingly, grew the best. Each point represents the average cell number/well of triplicate wells in a 24 well plate. The generation time for SH-SYSY was 24 hours in normal medium; this compared to 48 hours for ρ° 64/5 cells in medium containing pyruvate. The ρ° 64/5 cells reached the same final density as the parental line. Uridine alone, like cells that received no addition, did not support growth of ρ° cells and cell death was noted after three days of plating.

The ability of pyruvate alone to support growth indicates that the enzyme dihydroorotate dehydrogenase, essential to de novo synthesis of uridine, may still be active in ρ° cells of the present invention. Depletion of mtDNA has been shown to cause uridine auxotrophy in other ρ° cell isolates (4).

Rates of reversion from the ρ° phenotype were determined by plating 2×10$^6$ cells in a 75 cm$^2$ flask and culturing in uridine/pyruvate deficient selection medium. The viability dependence on uridine and pyruvate appeared within 2–3 weeks when most cells died. The very few surviving cells were then sub-cultured and designated as revertants. Reversion frequency as measured by survival under these conditions was 1×10$^{-5}$ for ρ° 33/5 clones and 1×10$^{-6}$ for ρ° 64/5 at 3 weeks (Table I). The very few surviving cells were subcultured. Activities of complex II, complex IV, citrate synthase and O$_2$ utilization returned to control levels in these subcultures, indicating that estimation of reversion by survival in selection medium was paralleled by return of ETC activity (Table I).

TABLE I

Respiratory and Biochemical Activities in Parental and ρ° Cells

| Cell | O$_2$ consumption nmol/min-mg (S.D.) | Complex IV min-mg$^{-1}$ (S.D.) | Complex II min-mg$^{-1}$ | Citrate Synthase min-mg$^{-1}$ | Reversion Rate |
|---|---|---|---|---|---|
| SH-SY5Y | 3.25 (0.57) | 2.025 (0.052) | 28.49 | 174.4 | |
| ρ° 33/5 | 0.21 (0.26) | 0.008 (0.003) | 30.69 | 158.2 | 10$^{-5}$ |

TABLE I-continued

Respiratory and Biochemical Activities in Parental and ρ° Cells

| Cell | $O_2$ consumption nmol/min-mg (S.D.) | Complex IV min-mg$^{-1}$ (S.D.) | Complex II min-mg$^{-1}$ | Citrate Synthase min-mg$^{-1}$ | Reversion Rate |
|---|---|---|---|---|---|
| ρ° 33/5 revertant | 3.72 (0.77) | 5.490 (0.281) | 29.58 | 167.4 | |
| ρ° 64/5 | 0.00 (0.28) | 0.048 (0.038) | 7.20 | 83.2 | $10^{-6}$ |

Note.
All activities are normalized to total cellular protein in mg.

Figure 4:
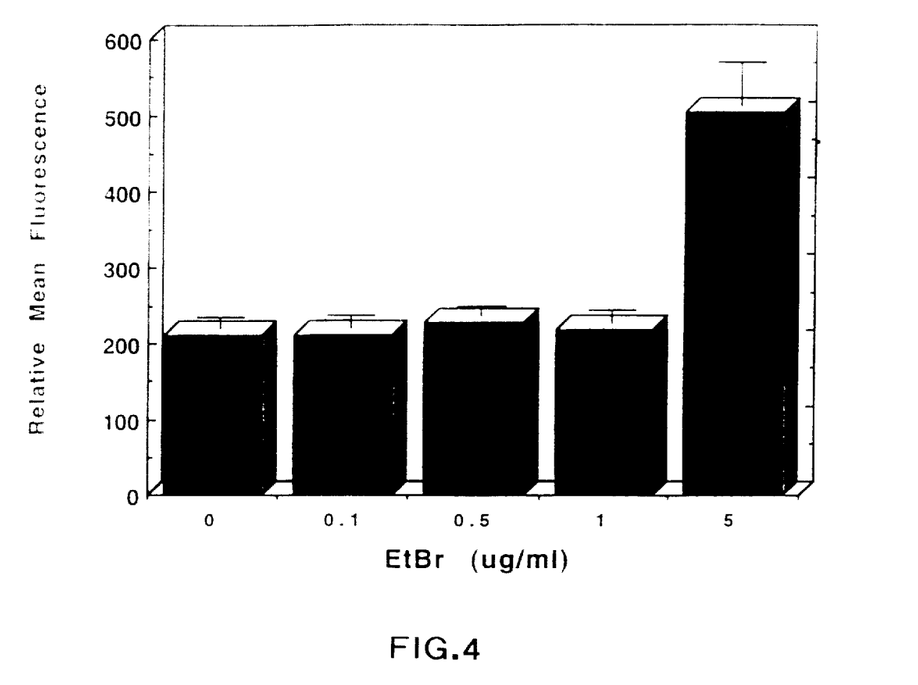
FIG. 4 is a graph showing that cells exposed to increasing concentrations of ethidium bromide for 64 days have increasing quantities of inner mitochondrial membrane, indicating that such cells have the large, irregular mitochondria that are characteristic of cells lacking mitochondrial DNA.

Binding of the fluorescent dye nonylacridine orange, was greatly increased in SH-SY5Y cells as a function of ethidium bromide exposure for 64 days, as shown in FIG. 4. Assay was performed in 96 well microplates; cells were plated at $2\times10^4$ cells per well 24 hours prior to the addition of 1 μg/ml nonyl acridine orange. Measurements were made as described above. Data are shown as the mean of 8 experiments±the standard deviation. Since nonylacridine orange binds selectively to cardiolipin, an inner mitochondrial membrane lipid, its uptake correlates with the number and size of the mitochondria (16,17). The data shown in FIG. 4 suggest that the ethidium bromide treated cells have increasing quantities of inner mitochondrial membrane, which would be expected, since cells lacking mitochondrial DNA have been observed to have large, irregular mitochondria (18).

Figure 5:
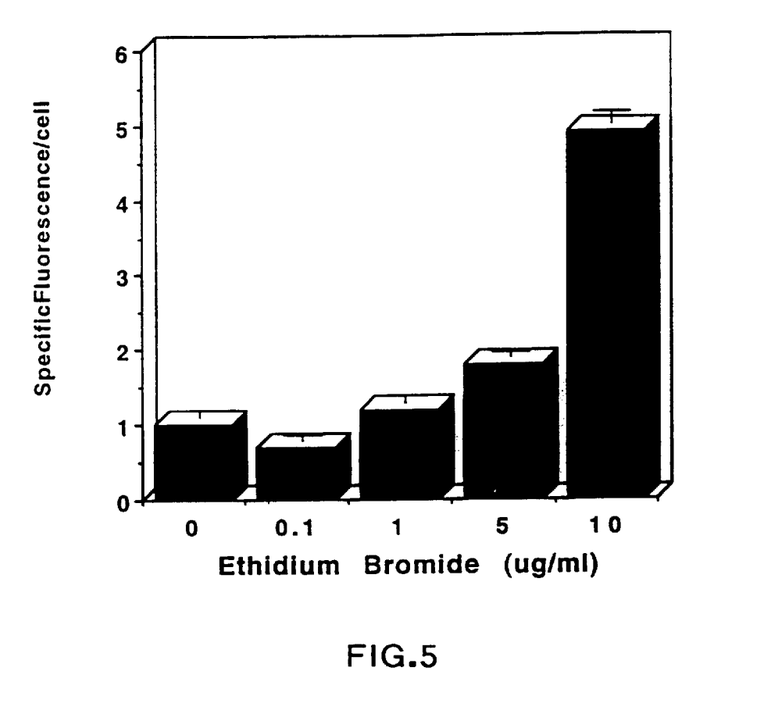
FIG. 5 is a graph showing that cells treated with ethidium bromide for 64 days and then treated with the cationic dye JC-1 show increased fluorescence, suggesting that the enlarged mitochondria establish increased transmembrane proton gradients even in the absence of mitochondrial DNA.

Similarly, as shown in FIG. 5, binding of the cationic dye JC-1 was also increased in ethidium bromide-treated cells. Measurements were made by fluorescent plate reader in 96 well microplates as described using 16 μM JC-1, and non-specific uptake was measured by concurrent addition of 5 μM CCCP. Cells were plated at $2\times10^4$ cells per well 24 hours prior to the addition of dye, and measurements were made as described above. Data are shown as the mean of 8 experiments±SD. Since JC-1 is known to equilibrate across the mitochondrial membrane as a function of the transmembrane electrical potential (19), the data shown in FIG. 5 indicate that the enlarged mitochondria expected in cells lacking mtDNA are able to establish increased transmembrane proton gradients, despite the lack of mitochondrial DNA, and despite the resulting lack of complex IV activity. This is consistent with the observed increase of nonyl acridine orange uptake (see above).

As a final further confirmation that the ρ° cells lack mtDNA, total DNA was extracted from untreated SH-SY5Y cells or SH-SY5Y cells exposed to ethidium bromide for 64 days at a concentration of 5 μg/ml, and mtDNA was analyzed by Southern blotting. Equal amounts of DNA were separated on agarose gels, transferred to nitrocellulose membranes, and hybridized with $^{32}$P-labelled mtDNA specific probe. SH-SY5Y ρ° cells had less than one mtDNA/cell when compared to a standard curve based on the known quantities of COX I gene (data not shown). This is essentially a finding of no detectable mtDNA, establishing conclusively that these cells were in the ρ° state.

The foregoing results suggest that the concentration of EtBr used to achieve the ρ° phenotype appears to be cell type specific. The parental neuroblastoma cell line needed high doses of EtBr (5 μg/ml) for long periods to induce the ρ° phenotype; dosages needed were 10 and 100 times greater than that need to produce ρ° fibroblast (17) and ρ° osteosarcoma cells (4), respectively. SH-SYSY cells may have high resistance to EtBr-induced toxicity. Of course, titrating the amount of ethidium bromide and the time needed for a given new type of cell is well within the average skill in the art.

It is important to note that in the case of neuroblastoma cells, once the ρ° phenotype appeared, continued treatment was necessary to obtain an acceptably low reversion rate, reversion being defined as the reappearance of the wild type phenotype when ρ° cells are grown without supplemented pyruvate. High reversion rates of ρ° cells fused with donor platelets would result in false positives during cybrid colony selection. An acceptable level of less than one reversion in $10^6$ was achieved after 64 days of EtBr treatment. Again, determining what duration of treatment is needed should be well within the average skill in the art.

Example 2
Differentiation of the Immortal ρ° Cells

The ρ° cells were induced to differentiate using phorbol ester (12-O-tetradecanoylphorbol-13-acetate, TPA) or growth factors. After two weeks of treatment with 16 μM TPA or 1 μM retinoic acid, the ρ° cells expressed long neurites with secretory granules typical of differentiating neuroblastoma cells. Thus, in contrast to the situation with ρ° cells derived from myoblasts, these neuroblastoma derived ρ° cells apparently retain the ability to differentiate as judged by morphologic criteria (21). This indicates that proteins encoded by the nuclear genes, essential to signal transduction and differentiation, are functional and not affected by EtBr treatment.

Example 3
Preparation of AD and PD Cybrids

ρ° 64/5 neuroblastoma cells were transformed with platelets from twelve Alzheimer's disease, three Parkinson disease and two age-matched control patients creating what are termed cybrid cells (ψ).

Platelets from AD and PD patients carrying mitochondria with single or multiple mutations in mtDNA encoding for ETC subunits, and from control (normal) patients, were isolated from 10 ml of whole blood drawn into an Becton Dickinson (Rutherford, N.J.) VACUTAINER containing anticoagulant (acid citrate dextrose). Samples of control SH-SY5Y cells were treated similarly. The samples were transferred into ACCUSPIN tubes (Sigma) over layers of HISTOPAQUE (Sigma), and centrifuged for 10 minutes at 1000×g at room temperature. The buffy coat containing both platelets and mononuclear lymphocytes was isolated, resuspended in five volumes of PBS and centrifuged at 1700×g for 10 minutes, decanted and resuspended in DMEM with 5 mM EDTA (fusion medium).

Transformation was accomplished by a modification of Chomyn et al (3). ρ° cells were removed from culture plates with trypsin, rinsed two times, and finally resuspended in fusion medium. ρ° cells ($4\times10^5$, clone ρ° 64/5.0) were combined with platelets ($1\times10^7$ platelets or $1\times10^8$ platelets)

in two mls of fusion medium and incubated 10 minutes at 37° C. Negative controls were ρ° cells without added platelets and platelets without added ρ° cells. The cell mixture was centrifuged at 300×g for 10 minutes, resuspended in 57 ml of fusion medium. Polyethylene glycol (70% w/v PEG 1000, J.T. Baker, McGraw Park, Ill.) in fusion medium was added to the cells to a achieve a final volume of 200 ml (final PEG concentration, 50%). Cells were incubated for 1.5 minutes at room temperature then diluted to a final volume of 10 mls with warm normal ρ° cell medium and allowed to recover for 10 minutes at 37° C. The fused cells were plated in 75 cm² flasks. The medium was changed on following day.

The cells were allowed to recover in ρ° medium for one week with medium changes every 2 days. Transformed cells (cybrids) repopulated with exogenous platelet mitochondria were selected by culturing in media lacking pyruvate and uridine with 10% dialyzed heat-inactivated FBS which removes residual uridine. These conditions were designed so that only repopulated cells could survive. The efficiency of transformation varied between 1 and 2% as judged by the number of surviving cells. Approximately $1 \times 10^3$ fused cells were plated sparsely onto a 15 cm. tissue culture dish.

Isolated colonies appeared 4 to 6 weeks after the initial fusion. Based on the calculated reversion rates observed for clonal ρ° 64/5.0 ($10^{-6}$) less than one spontaneously reverted clone should have appeared in these cultures. The aerobic phenotype is partially rescued by the transformation with mtDNA or mitochondria carrying mtDNA with specific mutations in the genes encoding for COX (disease phenotype).

Both the heterogeneous surviving cells (bulk phase) and isolated homogenous clones were propagated and assayed for complex I and IV activity and compared with complex I and IV activity from the parental SH-SY5Y cells (Table II). The complex IV defect associated with brain and blood of Alzheimer's disease (11,12) was successfully transferred to ρ° 64/5 neuroblastoma cells.

stable. Thus the defect transferred appears to be stably maintained for at least three cell passages and is probably permanent.

Since the fused cells displayed a specific decrease in complex I and IV enzymatic activity that is characteristic of AD and PD neuronal cells, these procedures provide a cellular model (AD and PD cybrid cells) for further study of a major biochemical and genetic defect found in the blood and brain of AD and PD patients.

Example 4
Screening of Drugs and Treatments Using AD Cybrids

The AD cybrid cells constitute a new and unique cellular model system.

To use this system to screen for drugs that are potentially useful in treating AD, the AD cybrids are grown in the presence of agents known or suspected of having the ability to ameliorate the electron transport deficit in AD patients, or the cellular degeneration that apparently results from that deficit. Alternatively, screening can be done in a completely empirical manner, and compounds for screening can be selected at random from those available anywhere in the world. Another alternative is to grow the cybrids in the presence of combinations of compounds, or subject them to other types of nutrients, vitamins, or other treatments.

After a period of treatment with a given compound, the treated cybrid cultures are tested to determine their COX activity relative to the COX activity of untreated cybrid control samples and normal cells, using methods such as those described hereinabove. In addition to measuring COX activity, treated and untreated cybrid controls observed microscopically to determine if the addition of the chemical agent has diminished the morphological changes characteristic of AD or PD. If treated cells exhibit an increase in COX activity and/or decrease in morphological degradation relative to untreated cybrids, the compound or compounds used in the treatment warrant further study to evaluate their potential effectiveness as drugs for treating AD. In addition, such positive results suggest that other similar chemical structures be screened for such activity.

TABLE II

Complex IV Activity of Control and Alzheimer's Disease Cybrids

| Cybrid | Patient Age | | Bulk Cells | Complex IV min-mg$^{-1}$ (S.D.) % reduction | Clones |
|---|---|---|---|---|---|
| SH-SY5Y | | | 2.025 (0.052) | — | |
| ψcon#0064 | 74 | | 1.963 (0.010) | 3.1 | 1.93 (0.73) |
| ψcon#0049 | 69 | | 2.862 (0.070) | −41.3 | 2.49 (0.69) |
| ψAD#2330 | 83 | week 1 | 1.500 (0.005) | 25.9 | 1.72 (0.99) |
| " | | week 2 | 1.762 (0.181) | 25.8 | |
| " | | week 3 | 1.432 (0.078) | 29.3 | |
| ψAD#2418 | 66 | | 1.520 (0.053) | 24.9 | 1.75 (0.47) |
| ψAD#2490 | 85 | | 1.375 (0.072) | 32.1 | 1.28 (0.24) |

The bulk phase of the three patients ψAD#2330, ψAD#2418 and ψAD#2490 had lower complex IV specific activities. The average deficit was 27.8%. The complex I defect associated with the brain and blood of Parkinson's disease also was successfully transferred to ρ° 64/5 neuroblastoma cells. The average deficit was 44.5%. The age-matched control cybrids, ψCon#0049 and ψCon#0064, had normal complex I and IV activity. The clones isolated from the bulk phase had similar values, but showed a high degree of variation. This may reflect various degrees of heteroplasmy within the clones. The complex IV activities of the bulk phase for ψAD#2418 were monitored for three weeks, consisting of three cell passages, and they continued to be Example 5

PD Cybrids

In a manner such as that described for construction of the AD cybrids, platelets from patients with Parkinson's disease and age-matched controls are fused with the ρ° cells described above, creating PD cybrids. Clones of individual cybrids are then isolated as described above, and their Complex I activities are measured by methods described previously in this application.

TABLE III

Comparison of Complex I and Complex IV Activity in Control and Parkinson's Disease Cybrids

| Cybrid | Complex I nmol/min/mg | Complex IV sec/mg |
|---|---|---|
| SH-SY5Y | 28.2 | 0.120 |
| Control 1 | 27.7 | 0.135 |
| Control 2 | 24.1 | 0.154 |
| Mean | 26.7 | 0.136 |
| Parkinson's Disease 1 | 18.3 | 0.110 |
| Parkinson's Disease 2 | 10.2 | 0.103 |
| Parkinson's Disease 3 | 15.9 | 0.188 |
| Mean | 14.8 | 0.134 |

Example 6
Preparation of AD Cybrid Animals

In another embodiment, mtDNA or mitochondria from diseased AD patients carrying specific multiple or single mutations in genes encoding for COX are introduced into animals, creating a mosaic animal.

A freshly fertilized mouse embryo, at about the 3 to 10 cell stage, is washed by saline lavage from the fallopian tubes of a pregnant mouse. Under a dissection microscope, the individual cells are teased apart, and are treated with ethidium bromide to induce a $\rho^\circ$ state, in a manner such as that described hereinabove. Determining the appropriate duration and concentrations for ethidium bromide treatment may require the sacrifice of several embryos for Southern analysis to assure that mitochondrial function has been lost.

Then, cells so treated are re-populated with exogenous mitochondria isolated from the platelets of an AD affected patient, the preparation of which is described in Example 3 above. One or more of the resulting cybrid cells are then implanted into the uterus of a pseudopregnant female by microinjection into the fallopian tubes. At the end of gestation, the COX activity of blood cells from one or more of the progeny is tested to confirm that the mitochondria behave as those of an AD patient. The presence of the AD COX gene defect can also be confirmed by DNA sequence analysis.

Example 7
Screening of Drugs and Treatments Using AD Cybrid Animals

Known or unknown agents are delivered to the cybrid animals, and agents that rescue the disease phenotype or protect against the deleterious consequences associated with the disease phenotype are selected for further study as potential drugs for the treatment of Alzheimer's Disease.

In addition, cells such as neurons and myoblasts can be isolated from these animals and used to screen for agents that rescue the disease phenotype or protect against the deleterious consequences associated with the disease phenotype. Such agents also should be further studied as potential treatments for Alzheimer's Disease.

BIBLIOGRAPHY

1. Wallace, D. C., 1992, Mitochondrial genetics: a paradigm for aging and degenerative diseases? Science 256:628–632.
2. Parker, W. D. Jr., Boyson, S. J., Parks, J. K. 1989, Abnormalities of the electron transport chain in idiopathic Parkinson's Disease, Am. J. Neurol. 26:719–723.
3. Chomyn, A., Lai, S. T., Shakeley, R., Bresolin, N., Scarlato, G., and Attardi, G., 1994, Platelet-mediated transformation of mtDNA-less human cells: analysis of phenotypic variability among clones from normal individuals and complementation behavior of the tRNA$^{lys}$ mutation causing myoclonic epilepsy and ragged red fibers, Am. J. Hum. Genet., 54:966–974.
4. King, M. P. and Attardi, G., 1989, Human cells lacking mtDNA: Repopulation with exogenous mitochondria by complementation, Science, 246:500–503.
5. Chomyn, A., Meola, G., Bresolin, N., Lai, S. T., Scarlato, G., Attardi, G., 1991, In vitro genetic transfer of protein synthesis and respiration defects to mitochondrial DNA-less cells with myopathy-patient mitochondria, Mol. Cell Biol. 11:2236–2244.
6. Biedler, J. L., Roffler-Tarlov, S., Schachner, M. and Freedman, L. S., 1978, Multiple neurotransmitter synthesis by human neuroblastoma cell lines and clones, Cancer Res., 38:3751–3757.
7. Van Den Bogert, C., Spelbrink, J. N. and Dekker, H. L., 1992, Relationship between culture conditions and the dependency on mitochondrial function of mammalian cell proliferation, J. of Cellular Physiol., 152:632–638.
8. Haas, R. H. and Stumpf, D. A., 1984, A microchamber for polarographic assay, Biochem. Med., 32:138–143.
9. Estabrook R. W., 1967, Mitochondrial respiratory control and the polarographic measurement of ADP:O ratios, Methods of Enzymol., 10:41–47.
10. Shepherd, D. and Garland, P. B., 1969, Citrate synthase from rat liver, Methods in Enzymol., 13:11–16.
11. Parker, W. D., Filley, C. F. and Parks, J. K., 1990, Cytochrome oxidase deficiency in Alzheimer's disease, Neurology, 40:1302–1303.
12. Parker, W. D. Jr., Parks, J., Filley, C. M., and Kleinschmidt-DeMasters, B. K., 1994, Electron transport chain defects in Alzheimer's disease brain, Neurology, 44: 1090–1096.
13. Lowry, O., Rosebouough, K., Farr, A. and Randall, R., 1951, Protein measurement with the folin phenol reagent, J. Biol. Chem., 193:265–275.
14. Ghosh, S. S., Kao, P. M., McCue, A. W. and Chappelle, H. L., 1990, Use of maleimide-thiol coupling chemistry for efficient syntheses of oligonucleotide-enzyme conjugate hybridization probes, Bioconjugate Chem., 1:71–76.
15. Desjardens, P., Frost, F. and Morais, R., 1985, Ethidium bromide-induced loss of mitochondrial DNA from primary chicken embryo fibroblasts, Mol. Cell. Biol., 5: 1163–1169.
16. Maftah, A., Petit, J. M. and Julien, R., 1990, Specific interaction of the new fluorescent dye 10-N-nonyl acridine orange with inner mitochondrial membrane, FEBS Letters, 260:236–240.
17. Leprat, P., Ratinaud, M. H., Maftah, A., Petit, J. M. and Julien, R., 1990, Use of nonyl acridine orange and rhodamine 123 to follow biosynthesis and functional assembly of mitochondrial membrane during L1210 cell cycle, Exp. Cell Res., 186:130–137.
18. Morais, R., Desjardins, P., Turmel, C. and Zinkewich-Peotti, K., 1988, Development and characterization of continuous avian cell lines depleted of mitochondrial DNA, In Vitro Cell. and Devel. Biol., 21:649–658.
19. Ehrenberg, B., Montana, V., Mei-De, W., Wuskell, J. P., Loew, L. M., 1988, Membrane potential can be determined in individual cells from Nemstain distribution of cationic dyes, Biophysical J., 53:785–794.
20. Johnson, L. V., Walsh, M. L., Bockus, B. J. and Chen, L. B., 1981, Monitoring of relative mitochondrial membrane potential in living cells by fluorescence microscopy, J. of Cell Biol., 88:526–535.
21. Herzberg, N. H., Zwart, R., Wolterman, R. A., Ruiter, J. P. N., Wanders, R., Bolhuis, P. A. and van den Bogert, C., 1993, Differentiation and proliferation of respiration-deficient human myoblasts, Biochim. et Biophys. Acta, 1181:63–67.

We claim:

1. An immortal and differentiatable human $\rho°$ cell line.

2. The immortal $\rho°$ cell line of claim 1, wherein said cell line is a $\rho°$ form of an immortal neural cell line.

3. The immortal $\rho°$ cell line of claim 1, wherein said cell line is a $\rho°$ form of a neuroblastoma cell line.

4. The $\rho°$ cell line of claim 3, wherein said cell line is a $\rho°$ form of neuroblastoma cell line SH-SY5Y.

5. A cybrid cell line comprising cultured immortal and differentiatable human cells having genomic and mitochondrial DNAs of differing human biological origins.

6. The cybrid cell line of claim 5, wherein said genomic DNA has its origin in an immortal and differentiatable $\rho°$ cell line, and said mitochondrial DNA has its origin in a human tissue sample.

7. The cybrid cell line of claim 6, wherein said human tissue sample is derived from a patient having a disease that is associated with a mitochondrial defect.

8. The cybrid cell line of claim 6, wherein said human tissue sample is derived from a patient having a disease that is associated with mitochondrial defects.

9. The cybrid cell line of claim 6, wherein said undifferentiated immortal $\rho°$ cell line is a $\rho°$ form of a neuroblastoma cell line and said human tissue sample is derived from a patient having a neurological disease that is associated with mitochondrial defects.

10. The cybrid cell line of claim 6 wherein said human tissue sample is from a patient having a disorder selected from the group consisting of Alzheimer's Disease, Parkinson's Disease, Huntington's disease, dystonia, Leber's hereditary optic neuropathy, schizophrenia, myoclonic-epilepsy-lactic-acidosis-and-stroke (MELAS), and myoclonic-epilepsy-ragged-red-fiber-syndrome (MERRF).

11. The cybrid cell line of claim 6, wherein said undifferentiated immortal $\rho°$ cell line is a $\rho°$ form of neuroblastoma cell line SH-SY5Y and said human tissue sample is from a patient having Alzheimer's Disease.

12. A differentiated cybrid cell line resulting from induction of differentiation in cells of the cybrid cell line of claim 6.

13. The cybrid cell line of claim 6, wherein said immortal $\rho°$ cell line is a $\rho°$ form of a neuroblastoma cell line.

14. The cybrid cell line of claim 13, wherein said neuroblastoma cell line is derived from the neuroblastoma cell line SH-SY5Y.

15. A method of constructing a differentiable neural human cybrid cell line, comprising the steps of:

a) treating an immortal cell line with an effective amount of a chemical agent which irreversibly disables mitochondrial electron transport and thus converting said cell line into an immortal differentiable $\rho°$ cell line; and b) transfecting said immortal differentiable cell line with isolated mitochondria to form said cybrid cell line.

16. The method of claim 15, wherein said isolated mitochondria are purified from a patient known to be afflicted with a disorder associated with a mitochondrial defect.

17. The method of claim 15, wherein said chemical agent is ethidium bromide.

18. A method of constructing differentiatable human cybrid cell lines, comprising the steps of:

a.) treating an immortal neuroblastoma cell line with ethidium bromide to irreversibly disable mitochondrial electron transport and thus convert said cell line into an immortal $\rho°$ neuroblastoma cell line; and b.) transfecting said immortal $\rho°$ neuroblastoma cell line with mitochondria isolated from tissue of a patient afflicted with a disorder selected from the group consisting of Alzheimer's Disease, Parkinson's Disease, Huntington's disease, dystonia, Leber's hereditary optic neuropathy, schizophrenia, myoclonic-epilepsy-lactic-acidosis-and-stroke (MELAS), and myoclonic-epilepsy-ragged-red-fiber-syndrome (MERRF), to form said cybrid cell line.

19. An immortal terminally differentiated human neural $\rho°$ cell line.

* * * * *

UNITED STATES PATENT AND TRADEMARK OFFICE
CERTIFICATE OF CORRECTION

PATENT NO.     :  5,888,498
DATED          :  March 30, 1999
INVENTOR(S)    :  Robert E. Davis and Scott W. Miller It is certified that error appears in the above identified patent and that said Letters Patent is hereby corrected as shown below:

Title Page:

Related U.S. Application Data delete:

"[63] Continuation-in-part of Ser. No. 219,842, Mar. 30, 1994, Pat. No. 5,565,323"

Signed and Sealed this

Twenty-second Day of August, 2000

Attest:

Q. TODD DICKINSON

*Attesting Officer*      *Director of Patents and Trademarks*

SEQUENCE LISTING ( 1 ) GENERAL INFORMATION:

( i i i ) NUMBER OF SEQUENCES: 1

( 2 ) INFORMATION FOR SEQ ID NO:1:

( i ) SEQUENCE CHARACTERISTICS:
( A ) LENGTH: 21 nucleotides
( B ) TYPE: nucleic acid
( C ) STRANDEDNESS: double
( D ) TOPOLOGY: linear ( x i ) SEQUENCE DESCRIPTION: SEQ ID NO:1:

CGTTTGGTAT TGGGTTATGG C 21